United States Patent [19]

Kato et al.

[11] Patent Number: 4,591,422

[45] Date of Patent: May 27, 1986

[54] ELECTROCHEMICAL OXYGEN SENSOR

[75] Inventors: Nobuhide Kato, Aichi; Takao Murase, Konan, both of Japan

[73] Assignee: NGK Insulators, Ltd., Japan

[21] Appl. No.: 709,803

[22] Filed: Mar. 8, 1985

[30] Foreign Application Priority Data

Mar. 16, 1984 [JP] Japan .............................. 59-38404[U]

[51] Int. Cl.[4] ...................... G01N 27/04; G01N 27/58
[52] U.S. Cl. .................................... 204/426; 204/428; 338/34
[58] Field of Search ................ 204/425, 426, 428, 1 S; 338/34

[56] References Cited

U.S. PATENT DOCUMENTS

| | | | |
|---|---|---|---|
| 4,098,653 | 7/1978 | Kita et al. | 204/1 T |
| 4,184,934 | 1/1980 | Bode et al. | 204/428 |
| 4,415,878 | 11/1983 | Novak | 338/34 |
| 4,479,866 | 10/1984 | Sone et al. | 204/425 |

Primary Examiner—G. L. Kaplan
Attorney, Agent, or Firm—Parkhurst & Oliff

[57] ABSTRACT

An oxygen sensor includes a planar oxygen sensing element having an oxygen detecting portion located in the vicinity of one end thereof, and a protective covering encloses the sensing element to protect the detecting portion in particular. The detecting portion has an oxygen detecting member exposed to a measurement gas. The sensing element has opposite primary surfaces having a larger area than other surfaces thereof, and the detecting member is disposed on the side of one of the primary surfaces. The protective covering has apertures for allowing the measurement gas to flow through a wall of the protective covering so that the detecting member is exposed to the measurement gas. The apertures are formed through a part of the wall of the protective covering which does not face the above-indicated one primary surface of the planar sensing element.

5 Claims, 6 Drawing Figures

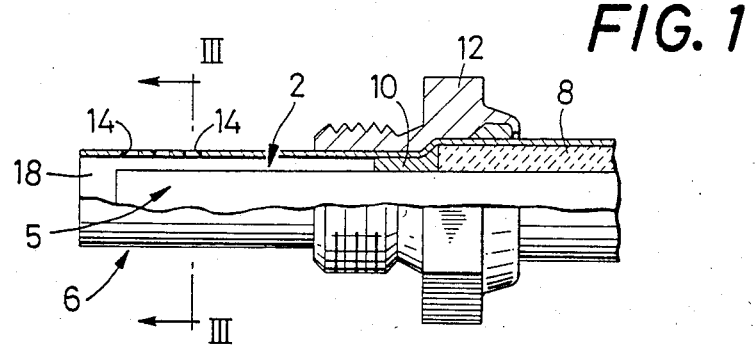
FIG. 1
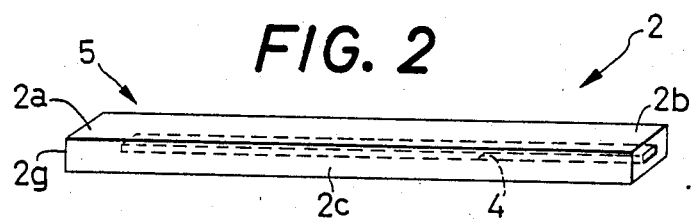
FIG. 2
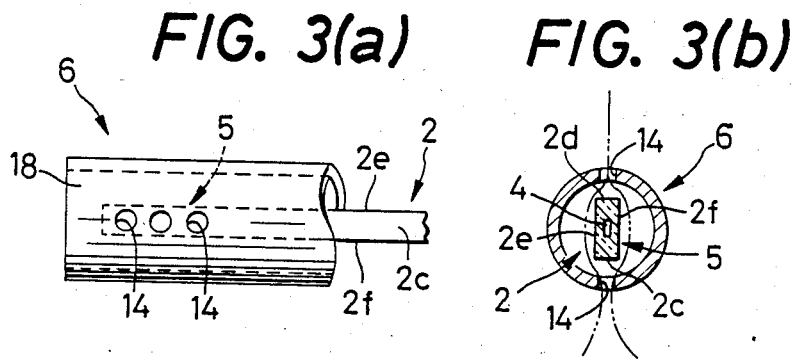
FIG. 3(a)   FIG. 3(b)
FIG. 4   FIG. 5
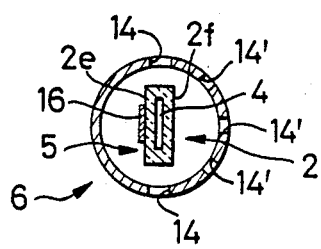
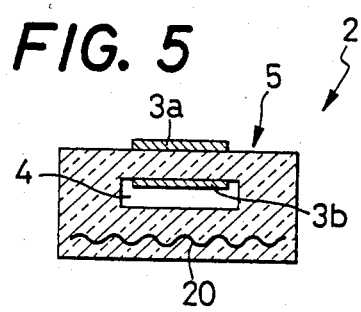

ELECTROCHEMICAL OXYGEN SENSOR

BACKGROUND OF THE INVENTION

The present invention relates generally to an oxygen sensor for detecting the oxygen concentration of a measurement gas, especially an exhaust gas produced by an internal combustion engine. More particularly, the invention is concerned with such an oxygen sensor which has a planar elongate sensing element, and a protective covering which encloses the sensing element to protect the same against direct exposure to the measurement gas.

An oxygen sensor has been known, which detects or determines the oxygen concentration of an exhaust gas emitted from internal combustion engines, for the purpose of controlling the cmbustion or fuel burning condition of the engine according to signals produced by the oxygen sensor, and thereby purifying the exhaust gas and saving the fuel consumption of the engine. An example of such oxygen sensor uses a sensing element which comprises a body of oxygen-ion conductive solid electrolyte such as zirconium oxide doped with calcium oxide or yttrium oxide, and further comprises suitable electrodes disposed on opposite surfaces of the solid electrolyte body. In this oxygen sensor, one of the electrodes is exposed to a reference gas while the other electrode is exposed to the exhaust gas. In operation, the oxygen sensor produces an output signal which represents an electromotive force induced between the two electrtodes according to the principle of an oxygen concentration cell. In recent years, there has been an increasing trend to use a planar elongate sensing element rather than a conventionally used tubular sensing element, in view of ease of manufacture and structural simplicity of the sensor. In an oxygen sensor using such a planar elongate sensing element, an oxygen detecting member to be exposed to an exhaust gas or other measurement gas, is disposed in an oxygen detecting portion of the sensing element, which portion is located adjacent to one end of the elongate sensing element. Another type of oxygen sensor is known in the art, which uses a sensing element including an elongate plate on which is provided an oxide such as titanium oxide, whose electrical resistance is varied in relation to the oxygen concentration of the exhaust gas or other measurement gas to which the sensing element is exposed. In operation, the oxygen sensor detects a variation in the electrical resistance of such oxide which represents the oxygen partial pressure of the measurement gas.

Oxygen sensors of various types as introduced above are installed such that their sensing element is partially inserted into a conduit through which an exhaust gas or other measurement gas is caused to flow, whereby the detecting portion of the sensing element, more precisely, the detecting member located at a surface of the sensing element, is exposed to the measurement gas. Generally, the oxygen sensor employs a protective covering member, usually of cylindrical shape in cross section, in order to enclose the sensing element for various purposes which include: to protect the element against thermal shock by high-temperature exhaust gas; to lower the temperature of the exhaust gas before it reaches the sensing element; and to prevent particles in the exhaust gas from being deposited on the sensing element.

The protective covering member has fluid-flow apertures in its cylindrical wall, so that the measurement gas flowing through the conduit is introduced into the protective covering member and brought into contact with the sensing element accommodated in the covering member. In this connection, it is required that the amount of flow of the measurement gas into the covering member for contact with the sensing element be held sufficient for detection of the oxygen concentration, but held to a minimum for protecting the sensing element. Namely, an excessive amount of flow of the gas into the covering member will result in early deterioration of the sensing element, i.e., shortened service life of the sensing element.

In a common oxygen sensor using a planar sensing element as previously indicated, a detecting member provided in a detecting portion of the sensing element in the vicinity of its one end is disposed in a very limited area of one of the opposite surfaces of the planar sensing element. This means that only a small amount of flow of the measurement gas into the protective covering member is required to accomplish the measurement of the oxygen concentration. In addition, the sensing element, more particularly its detecting member disposed in the small area is easily deteriorated if the structure of the protective covering member allows the measurement gas to flow directly against the detecting member.

In the known oxygen sensor using a planar sensing element, the sensing element is enclosed by a cylindrical protective covering member which has the same construction as a protective covering member used for a conventional tubular sensing element. Stated in more detail, the protective covering member enclosing the planar sensing element has fluid-flow apertures or openings over the entire circumference of its cylindrical wall. As a result, a large amount of the measurement gas, e.g., an exhaust gas flowing through an exhaust pipe, is introduced into the protective covering member such that not only the detecting member at the detecting portion at the end of the sensing element but also other portions of the element not carrying an electrode are directly exposed to streams of the gas. Consequently, various components of the oxygen sensing element such as a solid electrolyte body and platinum electrodes are unnecessarily deteriorated, and the life of the oxygen sensor is accordingly shortened. In addition to these problems, the known oxygen sensor of the type using a planar sensing element suffers another problem that the response of the sensor is affected by the position of the fluid-flow apertures or openings formed in the protective covering member, and by the circumferential position of the covering member with respect to the line of flow of the measurement gas through the conduit to which the sensor is attached.

SUMMARY OF THE INVENTION

The instant invention, therefore, has as its object the provision of an oxygen sensor with a protective covering for protecting a planar sensing element, which is so constructed as to protect the sensing element against deterioration due to exposure thereof to a measurement gas introduced through the wall of the protective covering, and prolong the service life of the sensor, and as to reduce a variation in the operating response of the sensor caused by the specific circumferential position of the sensor with respect to the line of flow of the measurement gas through a conduit to which the sensor is attached for detecting the oxygen concentration of the measurement gas.

According to the invention, there is provided an oxygen sensor including a planar oxygen sensing element having an oxygen detecting portion located in the vicinity of one end thereof, and further including a protective covering enclosing the sensing element to protect the detecting portion in particular, said oxygen detecting portion having thereon an oxygen detecting member exposed to a measurement gas, the planar sensing element having opposite primary surfaces having a larger area than other surfaces thereof, the detecting portion being disposed on the side of one of the primary surfaces, characterized in that the protective covering has fluid-path means for allowing the measurement gas to flow through a wall of the protective covering so that the detecting member of the sensing element is exposed to the measurement gas, the fluid-path means being formed through a part of the wall of the protective covering which does not face said one primary surface of the planar sensing element.

In the oxygen sensor constructed as described above, the fluid-path means permits the measurement gas to be introduced into the protective covering in a possible minimum amount necessary to effect the measurement or determination of the oxygen concentration of the measurement gas. The position of the fluid-path means relative to the sensing element is so determined as to prevent direct exposure of the detecting member of the sensing element to a stream of the measurement gas, and as to minimize deterioration of the sensing element due to such direct exposure. Thus, the arrangement of the fluid-path means in the protective covering relative to the sensing element according to the invention contributes to improvements in the service life and response characteristics of the oxygen sensor. In particular, the response of the sensor will be least affected by the specific circumferential position of the oxygen sensor, more precisely, by the circumferential position of the protective covering with respect to the line of flow of the measurement gas through a conduit to which the sensor is attached.

According to one embodiment of the invention, the fluid-path means comprises at least one aperture which is formed in a part of the wall of the protective covering which is opposite to one of opposite side surfaces of the sensing element that extend along the length of the sensing element. Preferably, the at least one aperture is located in the vicinity of the detecting portion of the sensing element.

In one form of the above embodiment, the at least one aperture comprises at least one aperture opposite to one of the opposite side surfaces of the sensing element, and at least one aperture opposite to the other side surface. According to an advantageous arrangement, a set of plural apertures are provided opposite to said one side surface and another set of plural apertures are provided opposite to the other side surface. The size of these apertures is selected to be smaller than the thickness of the planar sensing element, i.e., a distance between the opposite primary surfaces, so that a flow of the measurement gas introduced through the apertures will not directly collide against the detecting member (e.g., a measuring electrode) on the sensing element.

According to another embodiment of the invention, the fluid-path means further comprises an opening formed at one end of the protective covering on the side corresponding to the detecting portion of the sensing element.

In the case where the detecting member in the detecting portion is disposed on one of the opposite primary surfaces of the sensing element, the fluid-path means may further comprise at least one additional aperture which is formed in a part of the wall which is opposite to the other of the opposite primary surfaces.

According to an advantageous embodiment of the invention, the oxygen sensing element comprises a planar solid electrolyte body which, for example, consists essentially of zirconia, and electrodes disposed on the planar solid electrolyte body. In this instance, one of the electrodes serves as said detecting member of the sensing element exposed to the measurement gas. Further, the sensing element may incorporate an electrical heater.

In a preferred embodiment, the protective covering has a cylindrical wall through which the fluid-path means is formed. In this case, the cylindrical wall has said apertures(s) or additional apertures(s), and the end of the cylindrical wall on the side corresponding to the detecting portion of the sensing element defines the previously indicated opening. The measurement gas introduced in the protective covering is discharged through this opening.

In another embodiment of the invention, the cylindrical protective covering has an end wall at one end of the cylindrical wall on the side corresponding to the detecting portion of the sensing element. This end wall may be provided with at least one aperture through which the mesurement gas introduced in the protective covering is discharged.

According to a further embodiment of the invention, the fluid-path means comprises at least one aperture which is formed in a part of the wall of the protective covering which is aligned with an extension line of one of opposite side surfaces of the sensing element that extend along the length of the sensing element. This part of the wall in which the at least one aperture is formed, is located away from the detecting portion of the sensing element in a direction along the length of the above-indicated extension line, i.e., along the length of the side surface.

BRIEF DESCRIPTION OF THE DRAWING

These and other objects, and many of the attendant features and advantages of this invention will be readily appreciated as the same becomes better understood by reference to the following detailed description of illustrative embodiments when considered in connection with the accompanying drawing, in which:

FIG. 1 is a fragmentary view partly in cross section of one embodiment of an oxygen sensor of the present invention;

FIG. 2 is a perspective view of an example of an oxygen sensing element used in the oxygen sensor of FIG. 1;

FIG. 3(a) is a view illustrating gas-flow apertures formed in a protective covering enclosing the sensing element of FIG. 2, and FIG. 3(b) is a schematic cross sectional view taken along line III—III of FIG. 1;

FIG. 4 is a schematic cross sectional view corresponding to FIG. 3(b), showing another embodiment of the invention; and FIG. 5 is a schematic view in transverse cross section of an oxygen detecting portion of the sensing element of FIG. 2 located adjacent to its one end.

DETAILED DESCRIPTION OF THE PREFERRED EMBODIMENT

To further clarify the present invention, illustrative embodiments of the invention will be described in detail with reference to the accompanying drawing.

There is shown in FIG. 1 an oxygen sensor embodying the invention, which comprises an elongate planar oxygen sensing element of laminar structure generally indicated at 2. The planar sensing element 2 is formed of zirconia ceramics or other oxygen-ion conductive solid electrolyte materials. As illustrated in FIG. 2 on an enlarged scale, the sensing element 2 is an elongate body of rectangular shape in transverse cross section having a relatively small width. The sensing element 2 has a reference-gas passage 4 which is formed therein along the length of the elongate body. The reference-gas passage 4 terminates at a first end portion 2a (left-hand side end as viewed in FIG. 2) of the elongate body of the sensing element 2, and is held in communication with an ambient atmosphere which serves as a reference gas used for the sensor.

As is well known and illustrated in FIG. 5, the oxygen sensing element 2 has an outer electrode 3a which is disposed at the first end portion 2a such that it is exposed to an exhaust gas or other gases that are measured by the instant oxygen sensor. This outer electrode 3a is hereinafter referred to as "detecting member" of the sensing element 2. An inner electrode 3b is disosed in a portion of the sensing element 2 substantially in alignment with the outer electrode 3a, such that the inner electrode 3b is exposed to the reference gas in the reference-gas passage 4. In this specific embodiment, the first end portion 2a of the sensing element 2 at which the outer and inner electrodes 3a, 3b are disposed, forms a detecting portion 5 (FIG. 2) of the element 2. Suitable conductive leads extend from these outer and inner electrodes 3a, 3b toward a second end portion 2b (right-hand side end as seen in FIG. 2) of the sensing element 2, whereby electric signals from the electrodes 3a, 3b are fed to an external device. The sensing element 2 incorporates a suitable electrical heater 20, as known in the art, which heats portions (5) of the sensing element 2 at which the electrodes 3a, 3b are disposed. The heating of such portions (5) by the heater 20 makes it possible to reduce the required warming-up time before the sensor becomes stably operative after the start of exposure to the measurement gas such as an exhaust gas (e.g., after the start of a cold engine whose exhaust gas is detected by the sensor). Further, the heater 20 maintains the first end portion 2a (detecting portion 5) of the sensing element 2 at a desired temperature above a lower limit, even while the temperature of the measurement gas (e.g., exhaust gas) is not sufficiently high for intended operation of the sensor. Accordingly, the heater 20 permits the oxygen sensor to achieve stable and accurate measurement of an oxygen concentration of the measurement gas at any time.

The thus constructed planar sensing element 2 is accommodated in or enclosed by a cylindrical protective covering 6 made of a suitable metallic material. Described in more detail, the protective covering 6 supports the sensing element 2 therein via a ceramic insulator 8 and a heat-resistant sealing member 10 which are fitted in the protective covering 6, and through which the sensing element 2 extend, as shown in FIG. 1. In this manner, the sensing element 2 is fluid-tightly supported within the protective covering 6. In the meantime, the protective covering 6 is supported by an annular housing 12 such that the protective covering 6 (and the sensing element 2 therein) extends through the bore of the housing 12 so that the first end portion 2a (including the detecting portion 5) projects into a conduit (not shown) such as an exhaust pipe through which an exhaust gas is caused to flow. the oxygen sensor is secured to the fluid conduit by fixing the annular housing 12 to the conduit.

The protective covering 6 of the instant oxygen sensor, which covers the sensing element 2, has fluid-path means which is formed through a part or parts of the cylindrical wall which do not face the detecting member (3a). Stated more specifically, the cylindrical wall of the protective covering 6 has plural (three in this specific embodiment) fluid-flow apertures 14 which are formed in a part of the cylindrical wall which is opposite to a side wall 2c of the sensing element 2, more precisely, opposite to a portion of the side wall 2c adjacent to the first end portion 2a, as shown in FIGS. 3(a) and 3(b). Therefore, these fluid-flow apertures 14 are complementary to the first end portion 2a of the sensing element 2, and are spaced apart from each other in an axial direction of the protective covering 6. In another part of the cylindrical wall diametrically opposite to the above-indicated part, similar fluid-flow apertures 14 are formed so that they face a side wall 2d opposite to the side surface 2c, as indicated in FIG. 3(b). In other words, the two sets of fluid-flow apertures 14 are formed in diametrically opposite parts of the cylindrical wall of the protective covering 6, so that they do not face a surface 2e of the rectangular sensing element 2 on which the detecting member (3a) is disposed, nor face a surface 2f opposite to the surface 2e. These surfaces 2e, 2f are referred to as primary surfaces of the sensing element 2 which have a larger area than the other surfaces. It is understood that the opposite side surfaces 2c and 2d which face the apertures 14 extend along the length of the elongate sensing element 2 and are perpendicular to the primary surfaces 2e and 2f. It is also understood that the opposite primary surfaces 2e, 2f defines the thickness of the sensing element 2, while the opposite side surfaces 2c, 2d define the width of the sensing element 2. As shown in FIGS. 3(a) and 3(b), the size of each aperture 14, more specifically the diameter of each circular aperture 14, is determined to be smaller than the thickness of the sensing element 2. Further, the total area of the three apertures 14 facing the side wall 2c and that of the three apertures 14 facing the side wall 2d are determined to be substantially equal to each other.

Further, the protective covering 6 has an opening 18 at one end of the cylindrical wall on the side corresponding to the first end portion 2a of the sensing element 2. This opening 18 cooperates with the fluid-flow apertures 14 to constitute the fluid-path means which permits the measurement gas to flow into the protective covering 6 and to be discharged therefrom.

As indicated above, the apertures 14 and opening 18 are formed only in those parts of the protective covering 6 which are opposite to the side surfaces 2c, 2d and to an end surface 2g of the first end portion 2a, respectively. No apertures or openings are formed in other parts of the protective covering 6.

As previously indicated, the oxygen sensor having the protective covering 6 is installed so that the end portion of the protective covering 6 having the apertures 14 is exposed in a stream of an exhaust gas or other measurement gas flowing through a conduit to which the annular housing 12 is secured. In this condition, the measurement gas is introduced in a possible minimum amount into the protective covering 6 through the fluid-flow apertures 14 which are located opposite to the side surface 2d of the sensing element 2, as shown in FIG. 3(b). The introduced stream of measurement gas is split at the side surface 2d into two branch streams along the opposite primary surfaces 2e and 2f. The two branch streams of the gas are merged before they reach the apertures 14 of the protective covering 6 opposite to the side surface 2c of the sensing element 2. The gas is then discharged into the stream outside the covering 6, through the apertures 14 opposite to the side surface 2c. Simultaneously, the gas introduced in the protective covering 6 goes out through the opening 18 at the end of the covering 6.

Thus, the protective covering 6 permits only a limited amount of the measurement gas to be introduced through the apertures 14 opposite to the side surface 2d of the sensing element 2, thereby minimizing a direct adverse effect of the measurement gas on the solid electrolyte, electrodes and other components of the sensing element 2. Accordingly, the deterioration of those components is effectively restrained, and the service life of the oxygen sensor is prolonged to a significant extent.

It is noted that the three fluid-flow apertures 14 are disposed along a substantially straight line on each side of the elongate sensing element 2, and that the apertures 14 opposite to the side surface 2c are located symmetrically with respect to the apertures 14 opposite to the opposide side surface 2d. In this arrangement, the measurement gas is not directed to the sensing element 2 perpendicularly to the primary surface 2e or 2f, however the oxygen sensor is positioned circumferentially with respect to the line of flow of the measurement gas through the conduit to which the sensor is connected. In other words, the measurement gas is introduced through one of the two opposed sets of apertures 14 (through the apertures 14 opposite to either one of the opposite side surfaces 2c, 2d) into the protective covering 6. That is, the gas is always introduced toward one of the side surfaces 2c, 2d, irrespective of the circumferential position of the oxygen sensor relative to the direction of flow of the measurement gas through the conduit, i.e., relative to the conduit. Accordingly, the circumferential position of the oxygen sensor with respect to the line of flow of the gas through the conduit has a comparatively less influence on the response of the oxygen sensor. Stated differently, the oxygen sensor is assured of a relatively high response irrespective of the circumferential position of the sensor. Further, the opening 18 at the end of the protective covering 6 allows the introduced measurement gas to be discharged therethrough, thereby permitting a smooth flow of the gas along the length of the sensing element 2 and consequently improving the response of the sensor.

While the three fluid-flow apertures 14 in the above embodiment are formed in each of the diametrically opposite parts of the cylindrical wall 6 opposite to the corresponding side surfaces 2c, 2d of the sensing element 2, it is possible to change the number of the apertures 14, as required. Further, the size, spacing and other aspects of the apertures 14 are suitably determined, so that the object of the invention may be attained with intended operational effects.

In the illustrated embodiment, the protective covering 6 has the opening 18 at its end corresponding to the first end portion 2a of the sensing element 2. However, the above end of the protective covering 6 may be closed with an end wall. If desired, this end wall may have a suitable number of apertures or holes through which the measurement gas introduced in the covering 6 is discharged out into the conduit.

Although the protective covering 6 in the above embodiment has the fluid-flow apertures 14 only in the diametrically opposite parts of its cylinderical wall opposite to the side surfaces 2c, 2d of the sensing element 2, additional apertures 14' similar to the apertures 14 may be formed in another part of the cylinderical wall as shown in FIG. 4. More particularly, when a detecting member 16 (outer electrode) of the element 2 is disposed only on the primary surface 2e, the additional apertures 14' may be formed in a part of the cylinderical wall of the covering 6 which is opposite to the primary surface 2f. In this case, too, the detecting member or outer electrode 16 is protected against deterioration thereof due to direct exposure to streams of the measurement gas introduced in the protective covering 6.

In the illustrated embodiments, the sensing element 2 is positioned relative to the protective covering 6 such the apertures 14, 14' are opposite to parts of the side surfaces 2c, 2d adjacent to the first end portion 2a (detecting member 16). However, it is possible to position the sensing element 2 in the protective covering 6 such that the apertures 14, 14' are located away from the end surface 2g (first end portion 2a) of the sensing element 2 in the longitudinal direction of the element 2. It will be understood, in this instance, that the apertures 14, 14' are located in alignment with an extension line of the respective side surfaces 2c, 2d of the sensing element 2.

The sensing element 2 used in the illustrated embodiments uses a planar solid electrolyte body made of oxygen-ion conductive solid electrolyte and operates according to the principle of an oxygen concentration cell. It is appreciated, however, to use a sensing element provided with an oxygen detecting member which consists of an oxide such as titania, the electrical resistance of which is varied as a function of an oxygen concentration of the measurement gas.

It will be obvious that other changes, modifications and improvements of the present invention are possible to those skilled in the art in the light of the foregoing teachings, within the scope of the invention defined in the appended claims.

As discussed heretofore, the oxygen sensor having a protective covering according to the invention is characterized by the provision of fluid-path means formed in the protective covering, which fluid-path means comprises apertures formed through parts of the wall of the protective covering which do not face the primary surfaces of a sensing element enclosed by the protective covering. If required, the fluid-path means may further comprise an opening formed at the end of the protective covering corresponding to the end portion of the sensing element at which a detecting portion is disposed. The apertures permits the measurement gas to be introduced into the protective covering in a possible minimum amount necessary to effect the measurement or determination of the oxygen concentration of the measurement gas. As indicated above, the position of the apertures relative to the sensing element is so determined as to prevent direct exposure of the detecting member of the sensing element to streams of the measurement gas, and to minimize deterioration of the sensing element due to such direct exposure. Thus, the arrangement of the apertures and opening in the protective covering according to the invention contributes to improvements in the service life and response characteristics of the oxygen sensor. In particular, the response of the sensor will be least affected by the specific circumferential position of the oxygen sensor, more precisely, by the circumferential position of the protective covering with respect to the line of flow of the measurement gas through a conduit to which the sensor is attached. Thus, the present invention provides an improved oxygen sensor used for example as an exhaust gas sensor for controlling an air-fuel ratio of an internal combustion engine, and has a large industrial significance in the related fields of art.

What is claimed is:

1. An oxygen sensor including a planar oxygen sensing element including a first side surface having a thickness and a second side surface of substantially equal thickness, and an oxygen detecting portion located at one end thereof, and further including a protective covering enclosing the sensing element to protect at least the detecting portion, said oxygen detecting portion having thereon an oxygen detecting member which is exposed to a measurement gas, said sensing element having opposite primary surfaces which are larger in area than said first and second side surfaces thereof, said detecting member being disposed on a side of one of said primary surfaces, wherein the improvement comprises:

a first plurality of fluid-path apertures formed through said wall of said protective covering and facing said first side surface and a second plurality of fluid-path apertures formed through said wall of said protective covering and located opposite to said first plurality of fluid-path apertures, said second plurality of fluid-path apertures facing said second side surface, each of said first and second plurality of fluid-path apertures being smaller in size than said thickness of said first and second side surfaces to prevent said measurement gas from flowing directly onto said detecting member.

2. The oxygen sensor of claim 1, wherein another opening is provided at one end of said protective covering on the side corresponding to said detecting portion of said sensing element.

3. The oxygen sensor of claim 1, wherein said oxygen sensing element comprises a planar solid electrolyte body consisting essentially of zirconia, and electrodes disposed on said planar solid electrolyte body, one of said electrodes serving as said detecting member exposed to said measurement gas.

4. The oxygen sensor of claim 1, wherein id oxygen sensing element incorporates an electrical heater.

5. The oxygen sensor of claim 1, wherein said protective covering has a cylindrical wall through which said first and second plurality of fluid-path apertures are formed.

* * * * *